US012773243B2

(12) United States Patent
Firmbach et al.

(10) Patent No.: US 12,773,243 B2
(45) Date of Patent: Oct. 27, 2026

(54) DEVICE FOR HOLDING A TRANSMITTER ARRANGEMENT INTERACTING WITH AN IMAGE OR SIGNAL ACQUISITION DEVICE OF A SURGICAL NAVIGATION SYSTEM

(71) Applicant: Aesculap AG, Tuttlingen (DE)

(72) Inventors: Franz-Peter Firmbach, Emmingen-Liptingen (DE); Katharina Welte, Villingen-Schwenningen (DE); Martin Nonnenmann, Wurmlingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 19/234,538

(22) Filed: Jun. 11, 2025

(65) Prior Publication Data

US 2025/0387148 A1 Dec. 25, 2025

(30) Foreign Application Priority Data

Jun. 19, 2024 (DE) ..................... 10 2024 117 246.0

(51) Int. Cl.
*A61B 17/74* (2006.01)

(52) U.S. Cl.
CPC .................................... *A61B 17/74* (2013.01)

(58) Field of Classification Search
CPC ............ A61B 90/14; A61B 2090/3991; A61B 2090/3983
See application file for complete search history.

(56) References Cited

U.S. PATENT DOCUMENTS

| | | | |
|---|---|---|---|
| 6,767,153 | B1 | 7/2004 | Holbrook |
| 2010/0261998 | A1 | 10/2010 | Stiehl |
| 2016/0287263 | A1 | 10/2016 | Firmbach et al. |
| 2022/0265365 | A1 | 8/2022 | Redmond et al. |

FOREIGN PATENT DOCUMENTS

| | | | |
|---|---|---|---|
| CN | 108035965 | A | 5/2018 |
| DE | 10245287 | A1 | 4/2004 |
| DE | 102007055456 | B4 | 4/2010 |
| DE | 102013108678 | A1 | 3/2015 |
| DE | 102015105931 | A1 | 10/2016 |
| WO | 2017165920 | A1 | 10/2017 |

OTHER PUBLICATIONS

Search Report received in European Application No. 25183114.5, dated Oct. 30, 2025, with translation (18 pages).

*Primary Examiner* — Andrew Yang
(74) *Attorney, Agent, or Firm* — Christopher A. Rothe; CM Law

(57) ABSTRACT

A device for holding a transmitter arrangement in a surgical navigation system has a base part and a fastener insertable into bone. A joint arrangement, which is held on the base part, includes a head, a shaft and a receiving part. The shaft extends away from the head and carries the transmitter arrangement. The head and transmitter arrangement are fixable with respect to the receiver part in a desired orientation. The head has a surface with a plurality of first surface discontinuities. The receiver part has at least one second surface discontinuity configured to mate with each of the first surface discontinuities to fix the head in one of a plurality of orientations. The first surface discontinuities are distributed over the surface of the head in such a way that adjacent orientations are separated by an angle of at most 15°, measured from a center of the head.

20 Claims, 3 Drawing Sheets

DEVICE FOR HOLDING A TRANSMITTER ARRANGEMENT INTERACTING WITH AN IMAGE OR SIGNAL ACQUISITION DEVICE OF A SURGICAL NAVIGATION SYSTEM

CROSS-REFERENCE TO RELATED APPLICATION

This application claims priority to German Application No. 10 2024 117 246.0, filed on Jun. 19, 2024, the content of which is incorporated by reference herein in its entirety.

FIELD

The present disclosure relates to a device for holding an active or passive transmitter arrangement interacting with an image or signal acquisition device of a surgical navigation system in a surgical situation on a patient, comprising a base part and at least one fastening means which is to be inserted into a bone of the patient, in particular into a thigh bone or lower leg bone in the case of endoprosthetic hip or knee joint replacement, in order to position the base part in a fixed orientation relative to the bone during the surgical situation, and a joint arrangement held on the base part.

BACKGROUND

Such a device has been disclosed by the applicant, wherein the joint arrangement can be pivoted about two axes and fixed in position. However, only four rotational positions are possible around the upward-facing axis.

SUMMARY

The present disclosure is based on the task of further improving a device of the type described above in such a way that it can be manufactured in a cost-effective manner and that the surgeon has even greater freedom in the arrangement of the base part of the device on the patient's bone in the operating situation, wherein the device should also be easy and safe to operate.

In a device of the type mentioned, this task is solved according to the present disclosure in that the joint arrangement is designed with a head that is spherical in its basic geometry and a shaft extending away from it and carrying the transmitter arrangement, and with a two-component receiving part for the head, relative to which the head and thus the transmitter arrangement can be fixed in a desired orientation relative to the bone, and in that the head has, on its surface, projections that protrude radially outward, in particular rounded projections, or depressions that dip radially inward, in particular dome-shaped recesses, or flat facet sections, and in that the receiving part for the head has an inner section that is at least partially complementary in shape to this, such that the head can be fixed in one of a number of discrete, selectable orientations relative to the receiving part, wherein the projections, the depressions, or the facet sections are distributed over the surface of the head in such a way that discrete, selectable orientations located next to one another enclose an angle of at most 15° with respect to one another, measured from the center of the sphere.

Therefore, the joint arrangement should not aim for a precisely spherical surface geometry with concentric clamping, as the applicant considers this to offer insufficient security with regard to undesirable unintentional adjustability after a single fixation. This is because, especially with relatively low clamping force, it cannot be guaranteed that the desired orientation will not shift again. Instead, a form-fitting fixation between the head and the two-component receiving part of the joint arrangement should be used to achieve play-free orientation and fixation of the device. The fact that the discrete, selectable orientations have an angle of at most 15°, in particular at most 12°, and preferably at most 10°, means that a high degree of freedom can be achieved in positioning the base part on the bone in order to align the head with the transmitter arrangement in such a way that a plane in which the plurality of transmitters are located is approximately orthogonal to the main axis of the image acquisition device.

The at least one fastening means may be an anchor, a screw, or a threaded pin, which can be fixed in a clamping receptacle on the base part so that, after the fastening means has been inserted into the patient's bone, the base part can be fixed in position there.

It is furthermore advantageous that the at least one fastening means is long enough so that the base part can be placed 5.0-50 mm away from the bone surface.

As already indicated, it proves advantageous if the transmitter arrangement carries at least three, in particular four transmitters, which are arranged on intersecting legs in one plane, one leg being formed by the shaft extending away from the head or being attachable thereto directly or indirectly.

For form-fitting fixation of the head relative to the receiving part, it is not necessary for the multi-component receiving part to completely enclose the head, which would also restrict the swiveling movement of the shaft arranged on it. Rather, it proves to be advantageous and sufficient if, viewed in a sectional plane enclosing the shaft, the receiving part surrounds the head over an angle of at least 120°, in particular of at least 130°, in particular of at least 140°, in particular of at most 170°, in particular of at most 160°, in particular of at most 150°, and, viewed in a sectional plane extending orthogonally to the shank, surrounds the head over an angle of at least 30°, in particular of at least 40° and of at most 90°, in particular of at most 80°, in particular of at most 70°, in particular of at most 60°.

In principle, it is also conceivable and sufficient if the receiving part or each component of the receiving part only has a shape-complementary inner section area, which can, to a certain extent, enter into a positive-locking and force-locking clamping connection or fixing connection with projections, recesses, or facet sections of the head. However, it would also be conceivable for the entire inner side of the respective component of the receiving part to be designed to complement the surface of the head.

It may also be provided that the components of the receiving part can be tightened against each other, in particular by means of a screw connection, a toggle, or knee lever mechanism, wherein it is further advantageous if the components can be tightened against each other and released from each other without tools, i.e., purely by manual operation.

According to one embodiment of the present disclosure, the head has depressions on its surface, wherein the depressions may in particular be cylindrical, conical, or dome-shaped. Accordingly, at least one projection is provided on the inner section of the receiving part, which can engage completely or partially in a depression of the head positioned opposite it when the components of the receiving part are forced or tightened against each other with the head enclosed.

A screw connection, a toggle mechanism, or a knee lever mechanism can be used advantageously for this purpose.

According to a further embodiment of the present disclosure, it proves to be advantageous that the head has depressions on its surface, wherein the depressions in the head can be cylindrical, conical, or spherical in shape, and that at least one projection with a curved, in particular spherically curved, free end is formed on the inner section of the receiving part, and that a radius of curvature of the spherically curved free end is greater than a radius of the depressions in the region of the surface of the head. The fact that the nominal size of the free end of the projection of the receiving part is greater than the nominal dimension of the depressions on the surface of the head allows self-centering between the head and the receiving part, which proves to be convenient and therefore advantageous in practical use.

According to a further embodiment, it may be provided that force-actuable positioning pins protrude radially inwardly from the inner section of the receiving part, which pins are displaceable in the receiving part and can each at least partially engage in a radially inwardly recessed, in particular dome-shaped, depression in the head in order to fix the head in one of a number of discrete, selectable orientations relative to the receiving part. The use of force-actuated positioning pins, in particular spring-loaded positioning pins, with a rounded design allows for easy operation when adjusting or setting the head in the receiving part.

Here too, it may prove advantageous for the positioning pins to have a curved, in particular spherical curved, free end and for the radius of curvature of the curved free end to be greater than the radius of the depressions in the area of the surface of the head.

Following a further development that can be described as particularly advantageous, it is proposed that the two-component receiving part preferably has flushing channels that open inward in each of the components so that an intermediate space between the receiving part and the head can be cleaned by introducing flushing fluid outside the surgical situation.

Further features, details, and advantages of the present disclosure are apparent from the drawings and the following description.

DETAILED DESCRIPTION

Figure 1:
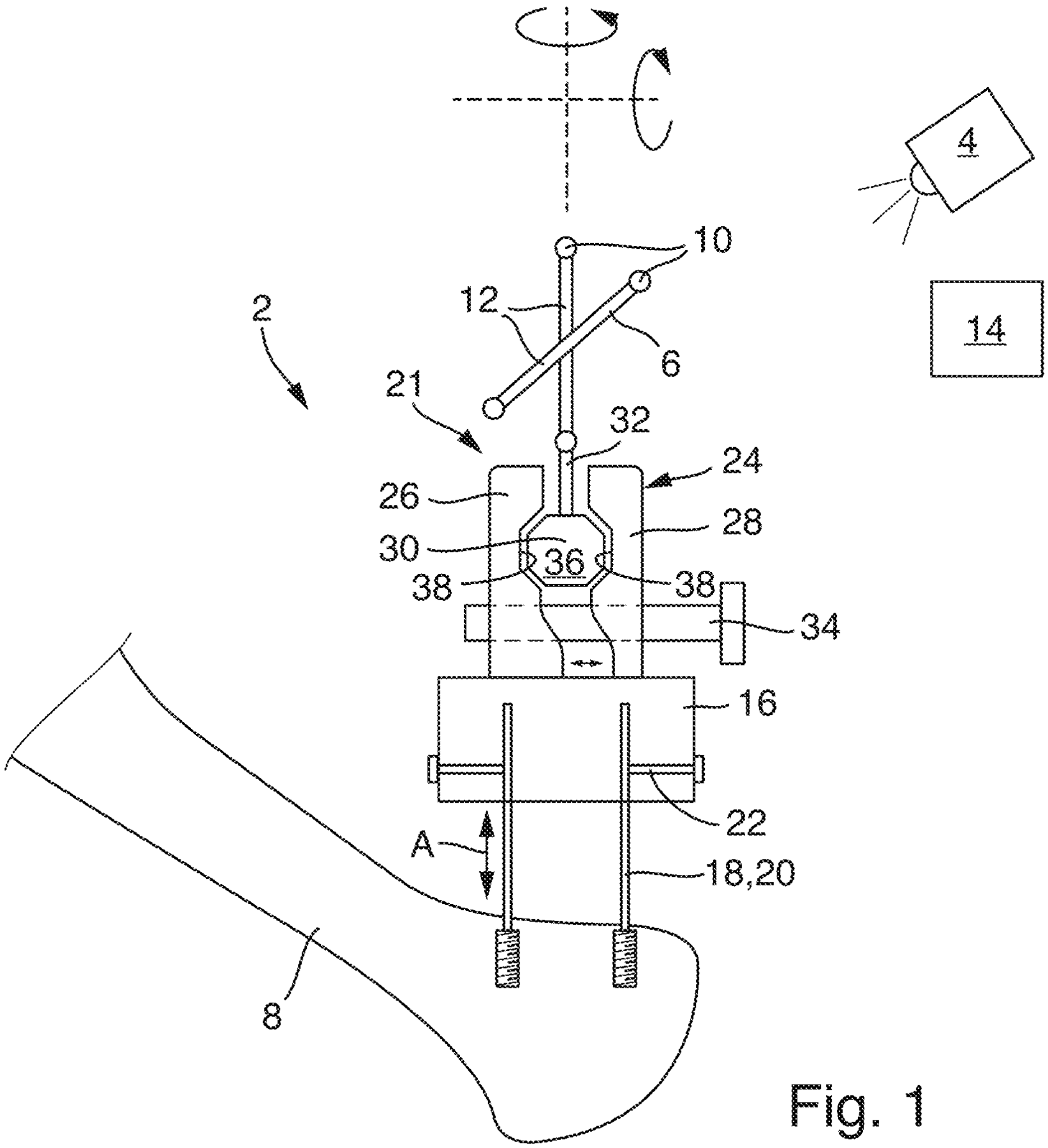
FIG. 1 is a schematic representation of a device according to the present disclosure for holding a transmitter arrangement in a surgical situation on a patient.

FIG. 1 shows a schematic representation of a device, designated overall by reference numeral 2, for holding a transmitter arrangement 6, which interacts with an image or signal acquisition device 4, in an operating room situation on a patient, namely on a bone 8 of the patient that is to be treated. The transmitter arrangement 6 preferably comprises a plurality of active or passive transmitters 10, which are arranged in an array in a plane which is formed in the present case by two legs 12 of the transmitter arrangement 6, to which the transmitters 10 are fixed. Signals emitted by the transmitters 10 or reflected by them are acquired by the image or signal acquisition device 4 and further processed in a computing device of the surgical navigation system, whereupon evaluations, suggested actions, and similar information for the surgeon are displayed on a display schematically designated by the reference numeral 14.

The device 2 comprises a schematically represented base part 16, which can be fixed to the bone 8 of the patient at a selectable distance from the bone by means of, for example, two fastening means 18 in the form of threaded pins 20. This is achieved by means of a respective clamping screw 22, which fixes the base part 16 relative to the relevant threaded pin 20.

The device 2 further comprises a joint arrangement 21 with a two-component receiving part 24, both components 26, 28 of which form a kind of clamping jaw for a head 30 which is spherical in its basic geometry. A shaft 32 extends from the head 30, which in the schematic representation merges into a leg 12 of the transmitter arrangement 6. The two components 26, 28 of the receiving part 24 can be moved toward or away from each other by means of a threaded spindle 34, so that the head 30 can be brought into a clamping position in the receiving part 24 or released again.

The head 30, which is shown schematically in FIG. 1, has projections on its surface 36 that extend radially outward and are particularly rounded, or depressions that extend radially inward and are particularly dome-shaped, or flat facet sections. Depending on the design, one and/or the other component 26, 28 of the receiving part 24 comprises an inner section 38 that is at least partially complementary in shape to the head 30, such that the head 30 can be fixed in a plurality of discrete, selectable orientations relative to the receiving part 24. Adjacent, separately selectable orientations form an angle of no more than 15° to each other, measured from the center of the sphere.

Figure 2:
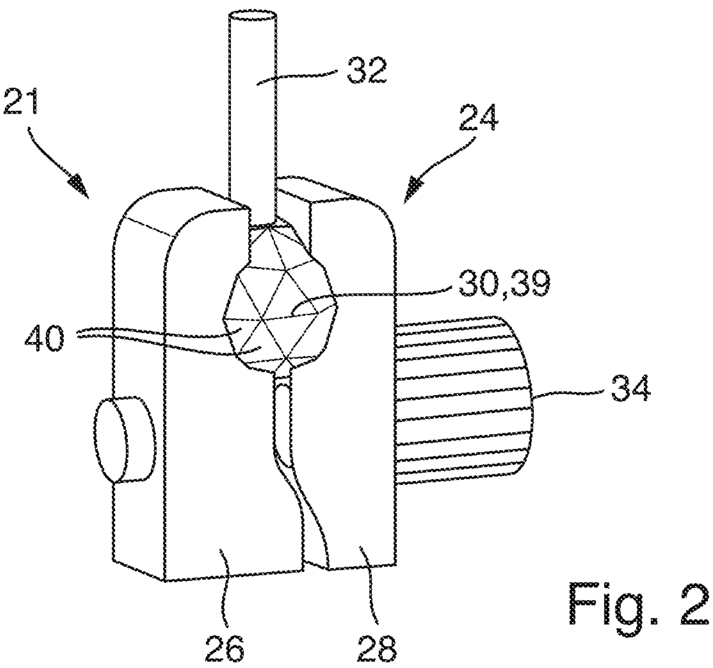
FIG. 2 is a perspective view of a joint arrangement of the device according to FIG. 1.
Figure 3:
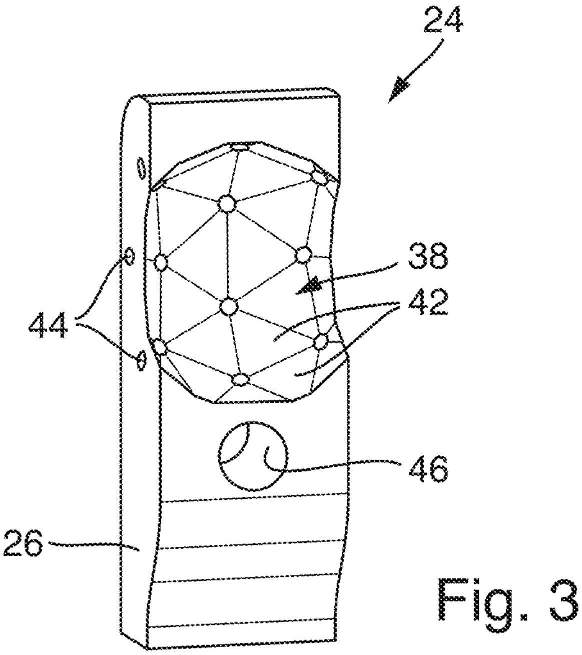
FIG. 3 is a perspective view of a component of a receiving part of the joint arrangement according to FIG. 2.

FIG. 2 illustrates a first embodiment of the device 2 according to the present disclosure in a merely schematic representation of the joint arrangement 21 with the two-component receiving part 24, the head 30 with the shaft 32 leading to the transmitter arrangement 6. In this embodiment, the head 30 comprises flat facet sections 40 on its surface 39. The two components 26, 28 of the receiving part 24 comprise a respective inner section 38 of complementary shape, which is shown in the component 26 in the top view in FIG. 3. It can be seen that the inner section also has facet sections 40 that are shaped and arranged to complement the facet sections 42. In addition, an embodiment is realized and indicated here, according to which flushing channels 44 are formed in the receiving part 24, which open into the inner section 38 of the receiving part 24. In this way, a space between the receiving part 24 and the head 30 can be flushed. Furthermore, FIGS. 2 and 3 illustrate the adjusting screw or threaded spindle 34, or a recess 46 for this purpose in the receiving part 24.

Figure 4:
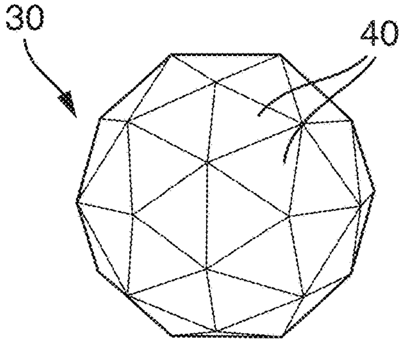
FIG. 4 is a perspective view of a head of the joint arrangement according to FIG. 2 with flat facet sections.

FIG. 4 again illustrates the head 30 with its flat facet sections 40.

Figure 5:
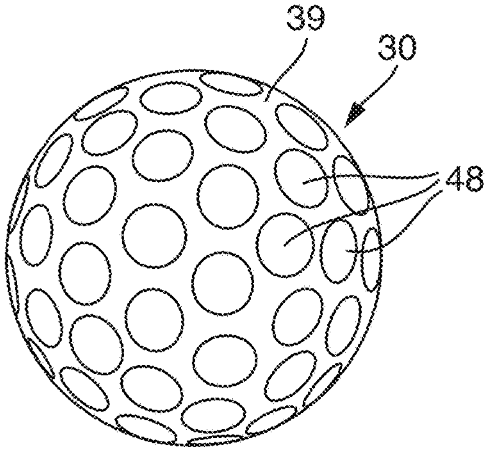
FIG. 5 is a perspective view of a further embodiment of a head of a further joint arrangement.
Figure 6:
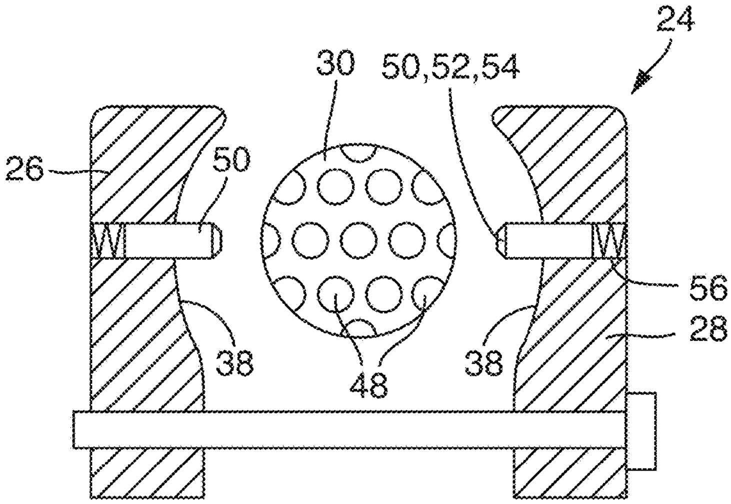
FIG. 6 is a schematic representation of an embodiment of a joint arrangement.

FIG. 5 illustrates another exemplary embodiment of the device according to the present disclosure, in which the head 30 is formed with radially inwardly recessed dome-shaped depressions 48, which are reminiscent of the surface structure of a golf ball. In the example shown, the depressions 48 are spherical, but this is not mandatory. In order to achieve a form-fitting and clamping fixation of the head 30 in a receiving part 24, which is only schematically shown in FIG. 6, a projection 50 extending radially inward is provided in the respective inner section 38 of the components 26, 28 of the receiving part 24, which is capable of engaging in the depressions 48 in the surface 39 of the head 30 when the head 30 is positioned accordingly. In the example shown, the projections 50 are formed by free ends 52 of pins 54 that can be acted upon by force, which is indicated schematically by the representation of a spring element 56.

Figure 7:
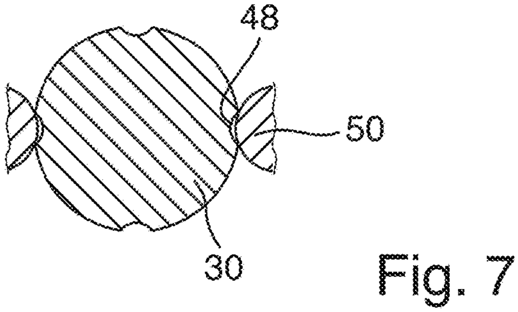
FIG. 7 is a schematic illustration of different nominal dimensions for partially interlocking projections and depressions on a receiving part and a sphere of a joint arrangement.

Finally, FIG. 7 again schematically illustrates that a nominal dimension or radius of curvature of inwardly extending projections 50 on the receiving part 24 may be greater than a nominal dimension of inwardly recessed depressions 48 on the head 30. This achieves a self-centering effect.

The device 2 described here in its various embodiments proves to be user-friendly and can be used in the operating room with minimal risk of malfunction. Due to the arrangement of the positively interacting depressions, projections, or facet sections of the sphere on the one hand and the complementary shape of the inner section of the components of the receiving part on the other, a large number of discretely selectable orientations of the sphere and thus of the transmitter arrangement can be selected and fixed, so that an orientation that is not step-free but is available in a narrow grid can be selected.

The invention claimed is:

1. A device for holding a transmitter arrangement interacting with an image or signal acquisition device of a surgical navigation system during a surgical procedure on a patient, the device comprising:

a base part;

at least one fastener insertable into a bone of the patient in order to position the base part in a fixed orientation relative to the bone during the surgical procedure; and a joint arrangement held on the base part, the joint arrangement comprising a head and a shaft extending away from the head, with the shaft carrying the transmitter arrangement, the joint arrangement further comprising a receiving part for the head, the head and the transmitter arrangement being fixable with respect to the receiving part in a desired orientation relative to the bone, the head comprising an outer surface having a plurality of first surface discontinuities, the receiving part comprising an inner section having at least one second surface discontinuity that is complementary to each of the plurality of first surface discontinuities, and each of the plurality of first surface discontinuities being selectively engageable with the at least one second surface discontinuity such that the head is fixable to the receiving part in a plurality of selectable orientations relative to the receiving part.

2. The device according to claim 1, wherein the plurality of first surface discontinuities are distributed over the outer surface of the head in such a way that adjacent orientations of the plurality of selectable orientations are separated by angle measured from a center of the head.

3. The device according to claim 2, wherein the angle is at most 15°.

4. The device according to claim 1, wherein:

the plurality of first surface discontinuities comprise rounded projections extending radially outwardly from the head, and the at least one second surface discontinuity comprises rounded recesses.

5. The device according to claim 1, wherein:

the plurality of first surface discontinuities comprise rounded recesses extending radially inwardly into the head, and the at least one second surface discontinuity comprises rounded projections.

6. The device according to claim 1, wherein:

the plurality of first surface discontinuities comprise a first plurality of flat facets extending around the outer surface of the head, and the at least one second surface discontinuity comprises a second plurality of flat facets.

7. The device according to claim 1, wherein the at least one fastener is an anchor, a screw, or a threaded pin.

8. The device according to claim 1, wherein the at least one fastener is fixable in a clamping receptacle on the base part so that, after the at least one fastener has been inserted into the bone, the base part is fixable in position.

9. The device according to claim 1, wherein the at least one fastener has a length such that the base part is arrangeable at a distance of 5.0-50 mm from a surface of the bone.

10. The device according to claim 1, wherein the shaft is configured to form a leg of the transmitter arrangement, the leg extending away from the head or attachable to the head in a direct attachment or an indirect attachment.

11. The device according to claim 1, wherein the receiving part, viewed in a sectional plane enclosing the shaft, surrounds the head at an angle of at least 120°.

12. The device according to claim 11, wherein the receiving part, viewed in a sectional plane extending orthogonally to the shaft, surrounds the head by an angle of at least 30°.

13. The device according to claim 1, wherein the receiving part comprises at least two components configured to be tightened against each other and around the head.

14. The device according to claim 13, wherein the at least two components of the receiving part are configured to be tightened against each other by a screw connection, a toggle or knee lever mechanism.

15. The device according to claim 14, wherein:

the plurality of first surface discontinuities comprise recesses extending radially inwardly into the head, the at least one second surface discontinuity comprises a projection configured to engage completely or partially in one of the recesses when the at least two components of the receiving part are tightened against each other and around the head.

16. The device according to claim 15, wherein:

the projection is formed with a curved free end having a first radius of curvature, each recess is rounded and has a second radius of curvature, and the first radius of curvature is greater than the second radius of curvature.

17. The device according to claim 1, further comprising positioning pins that are radially inwardly forceable, the positioning pins protruding from the inner section of the receiving part and being displaceable in the receiving part, each positioning pin configured to at least partially engage one of the plurality of first surface discontinuities on the head in order to fix the head in one of the plurality of selectable orientations relative to the receiving part.

18. The device according to claim 17, wherein:

each of the plurality of first surface discontinuities comprises a recess having a first radius of curvature, and each positioning pin has a curved free end having a second radius of curvature greater than the first radius of curvature.

19. The device according to claim 1, wherein the receiving part comprises flushing channels configured to receive a flushing fluid to clean an intermediate space between the receiving part and the head.

20. The device according to claim 1, wherein the head which is spherical in shape.

* * * * *